(12) United States Patent
Talwar et al.

(10) Patent No.: US 9,675,247 B2
(45) Date of Patent: Jun. 13, 2017

(54) ALPHA-MATTING BASED RETINAL VESSEL EXTRACTION

(71) Applicants: Powel Talwar, Menlo Park, CA (US); Mithun Das Gupta, Menlo Park, CA (US)

(72) Inventors: Powel Talwar, Menlo Park, CA (US); Mithun Das Gupta, Menlo Park, CA (US)

(73) Assignee: RICOH CO., LTD., Tokyo (JP)

(*) Notice: Subject to any disclaimer, the term of this patent is extended or adjusted under 35 U.S.C. 154(b) by 0 days.

(21) Appl. No.: 14/562,300

(22) Filed: Dec. 5, 2014

(65) Prior Publication Data

US 2016/0163041 A1 Jun. 9, 2016

(51) Int. Cl.
| | |
|---|---|
| G06T 7/00 | (2006.01) |
| G06T 5/00 | (2006.01) |
| A61B 3/14 | (2006.01) |
| A61B 3/12 | (2006.01) |
| A61B 3/00 | (2006.01) |
| G06F 19/00 | (2011.01) |
| G06T 7/11 | (2017.01) |
| G06T 7/194 | (2017.01) |
| G06T 7/136 | (2017.01) |

(52) U.S. Cl.
CPC .............. *A61B 3/14* (2013.01); *A61B 3/0025* (2013.01); *A61B 3/1241* (2013.01); *G06F 19/321* (2013.01); *G06T 7/11* (2017.01); *G06T 7/136* (2017.01); *G06T 7/194* (2017.01); *G06T 2207/30041* (2013.01); *G06T 2207/30101* (2013.01)

(58) Field of Classification Search
None
See application file for complete search history.

(56) References Cited

U.S. PATENT DOCUMENTS

| | | | | |
|---|---|---|---|---|
| 2007/0230810 A1* | 10/2007 | Kanatsu | ............. | G06K 9/00456 382/243 |
| 2008/0267525 A1* | 10/2008 | Dai | ........................ | G06T 3/403 382/266 |
| 2009/0213439 A1* | 8/2009 | Miyamura | ............ | G06T 7/0081 358/474 |
| 2010/0061628 A1* | 3/2010 | Yamada | ................ | G06T 7/0081 382/167 |
| 2010/0302376 A1* | 12/2010 | Boulanger | ............ | G06T 7/0097 348/164 |

(Continued)

OTHER PUBLICATIONS

Richard Szeliski, Computer Vision: Algorithms and Applications, Aug. 18, 2010 draft, p. 105.*

(Continued)

*Primary Examiner* — Jason Heidemann
*Assistant Examiner* — Brian Shin
(74) *Attorney, Agent, or Firm* — Blakely, Sokoloff, Taylor & Zafman LLP

(57) ABSTRACT

Retinal vessel extraction on color images of eyes are disclosed. In one embodiment, the method comprises performing alpha matting on a multi-dimensional feature set derived from image data of a first image and performing retinal vessel extraction, including performing segmentation on the image by separating foreground and background image data from the first image using an output from the alpha matting.

20 Claims, 10 Drawing Sheets

(56) References Cited

U.S. PATENT DOCUMENTS

2012/0063660 A1* 3/2012 Imamura .............. A61B 5/0066
                                                    382/131
2014/0079296 A1* 3/2014 Cleland ................. G06F 21/32
                                                    382/117

OTHER PUBLICATIONS

Zhang et al., Retinal vessel extraction by matched filter with first-order derivative of Gaussian, Jul. 25, 2009, Published in Computers in Biology and Medicine, pp. 438-445.*

* cited by examiner

ALPHA-MATTING BASED RETINAL VESSEL EXTRACTION

FIELD OF THE INVENTION

Embodiments of the present invention relate to the field of blood vessel extraction from retinal images; more particularly, embodiments of the present invention relate to alpha-matting based retinal vessel extraction.

BACKGROUND OF THE INVENTION

Study of characteristics of the vasculature of eye provides useful insights to many ophthalmic disorders. The properties of vasculature such as width, length, branching pattern, and ratio of size of optic disk to size of optic cup are important parameters in detection of retinopathies, hypertension, glaucoma, and vein or artery occlusion. Early and regular screening of eye can help in timely detection and treatment of most of these problems. The manual examination of a large number of retinas by doctors to search for the symptoms is a labor intensive process. It has been established that automatic delineation of blood vessels in a retina can be very helpful in diagnosing, screening and treatment of such diseases. Thus, automatic extraction of retinal maps forms an important first step in establishing any computer aided diagnostic system for ophthalmic disorders.

Numerous methods have been used to segment the blood vessels from retina color images. These methods can be classified as supervised and unsupervised. Supervised methods usually have higher accuracy than unsupervised variants but require generation of high quality training data. Unsupervised methods have no such requisites and thus find greater application where training data is difficult to produce. A supervised learning algorithm using a large number of features for training has been proposed. This proposed methodology is based on ridge extraction to find location of vessels. The ridges are used to compose primitives in the form of line segments. The image is then partitioned into patches by assigning each pixel to the nearest line segment. Feature vectors are calculated for each pixel and classified using a KNN classifier. Another prior art technique uses Gabor feature based supervised learning for vessel segmentation. A Morlet wavelet transform has been used to extract features at different scales. Another technique uses grey intensity values and Hu's moments calculated on the image as features, and these are fed to a neural network for classification. In another technique, line detectors and Support Vector Machines are used to classify pixel as vessel or non-vessel. Recently, a vector divergence field approach has been proposed to handle bright lesions and obtained high accuracy. Another technique uses response towards Gaussian profile and first order derivative of Gaussian filter to differentiate between vessel and non-vessel regions. Yet others have used pixel classification methods to segment image into vessels and non-vessels.

SUMMARY OF THE INVENTION

A method and apparatus for performing retinal vessel extraction are disclosed. In one embodiment, the method comprises performing alpha matting on a multi-dimensional feature set derived from image data of a first image and performing retinal vessel extraction, including performing segmentation on the image by separating foreground and background image data from the first image using an output from the alpha matting.

Embodiments of the present invention can take other forms such as other systems, methods, articles of manufacture, and computer readable storage media.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

Figure 1:
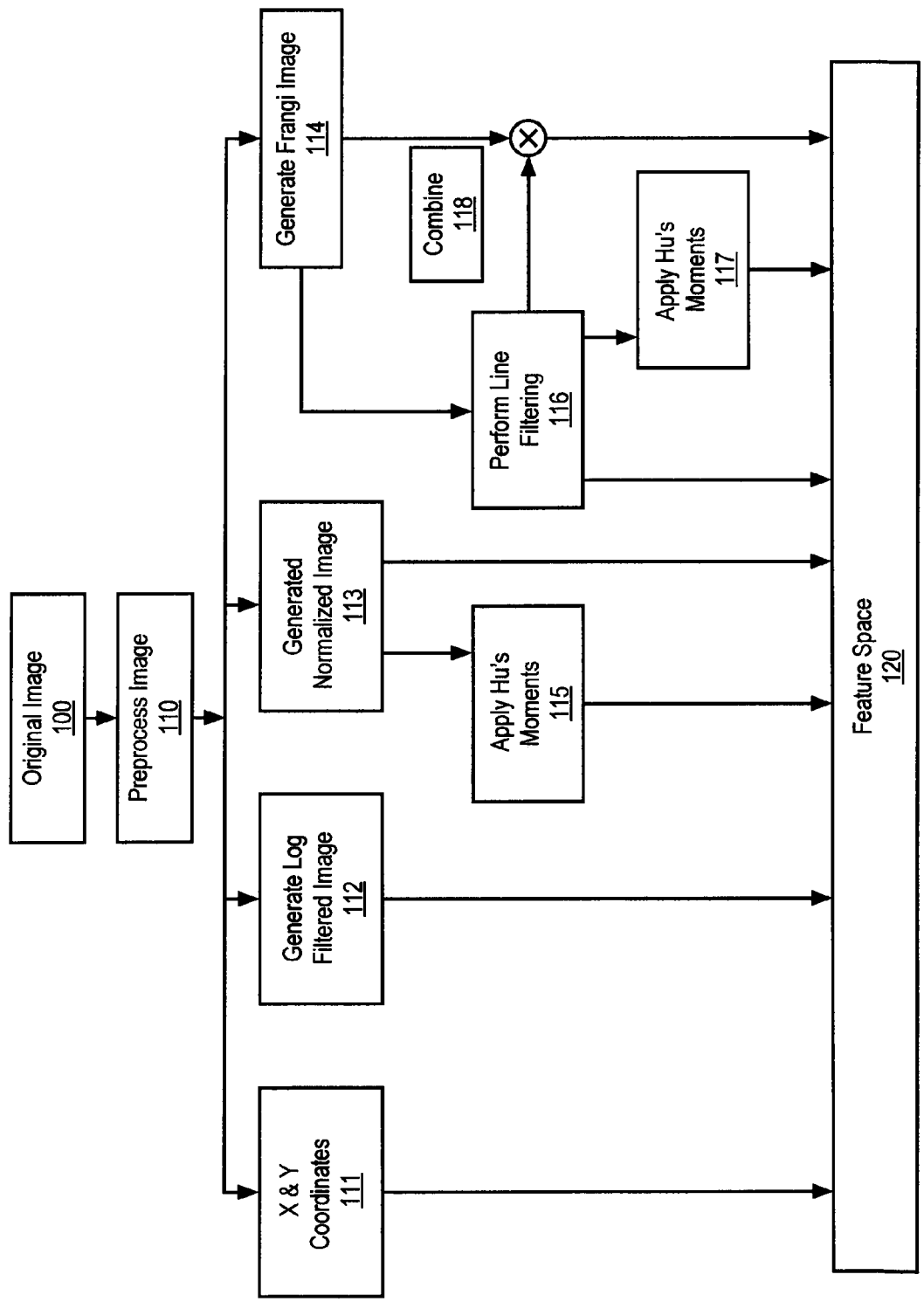
FIG. 1 is a flow diagram of one embodiment of a process for creating a multi-dimensional feature space.

A technique for blood vessel extraction in fundus color images of the eye using an alpha-matting technique is described. In one embodiment, the alpha-matting technique is a K-nearest neighbors (KNN) based alpha-matting and is used to separate vessel and non-vessel regions in an image. In one embodiment, larger blood vessels are used to generate the tri-map needed for matting. Therefore, in one embodiment, no input is required from the user to generate the tri-map. A multi-dimensional feature set is constructed and fed into the matting framework. The affinities among the pixels are used to obtain the matting Laplacian, whose eigen decomposition leads to segregation of the vessel and non-vessel regions in the image having retinal vessels.

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Some portions of the detailed descriptions which follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A non-transitory machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; etc.

Overview

A method for retinal vessel extraction is described. In one embodiment, the technique is described herein can efficiently handle the task of segmenting out blood vessels and reduce the effect of Central Vessel Reflex to a great extent. In one embodiment, the vessel extraction technique is based on an alpha-matting technique that is used to separate foreground and background in an image. In one embodiment, the alpha matting technique is well known in the art. For more information on the K Nearest Neighbor (KNN) technique for matting, see Chen & Tang, "KNN matting," in *IEEE CVPR*, 2012, pp. 869-876. The KNN method finds the K nearest neighbors in a non-local neighborhood from the multi-dimensional feature space and creates a matting Laplacian from which the foreground and background of an image can be separated. No user inputs are needed for the alpha matting. As part of the usual extraction process, tri-map generation is performed. A tri-map is an image with user marked annotations or scribbles to mark regions as sure foreground or background and unknown regions. In one embodiment, tri-map generation is done automatically from the generated features.

In one embodiment, the processing comprises generating a multi-dimensional feature set by applying one or more of operations of a set of operations on the image data of the first image or data derived from the image data of the first image, performing alpha matting on a multi-dimensional feature set derived from image data of a first image; and performing retinal vessel extraction, including performing segmentation on the image by separating foreground and background image data from the first image using an output from the alpha matting. In one embodiment, the alpha matting comprises K-nearest neighbor (KNN) based alpha matting, and includes performing an Otsu segmentation process to the output of the alpha matting.

In one embodiment, the multi-dimensional feature set is generated by applying one or more of the following operations: generating a filtered image by applying a Laplace of Gaussian (LoG) filter to the first image; generating a normalized image from the first image; generating a Frangi image from the first image; applying line filtering to the Frangi image to create a line filtered image; multiplying the line filtered image with the Frangi image; calculating Hu's moments on the line filtered image; and calculating Hu's moments on the normalized image. In one embodiment, all of these operations are applied to create a feature set that is then used in the alpha matting process.

Generating a Multi-Dimensional Feature Set

In one embodiment, the retinal vessel extraction process begins by creating a multi-dimensional feature set. The feature set may then be input into the alpha matting process.

FIG. 1 is a flow diagram of one embodiment of a process for creating a multi-dimensional feature space. The process is performed by processing logic that may comprise hardware (circuitry, dedicated logic, etc.), software (such as is run on a general purpose computer system or a dedicated machine), firmware, or a combination of the three.

Referring to FIG. 1, the process begins by performing preprocessing on an original image 100 (processing block 110). Color fundus images invariably show important intensity variations, poor contrast and noise. In one embodiment, the preprocessing includes filtering and other operations performed on the input image. For example, in one embodiment, the preprocessing includes noise filtering to remove granular noise. In one embodiment, the noise filtering is accomplished by using Wiener filtering. In one embodiment, a Weiner filter is applied over a 3×3 window to remove granular and speckle noise from the image.

In one embodiment, the preprocessing includes performing contrast enhancement of the retina images. The contrast enhancement is performed on the input image or an input image that has already undergone noise removal. In one embodiment, the contrast enhancement is accomplished by applying filter to the image. In one embodiment, the filter that is applied to the image is a Laplacian of Gaussian (LoG) filter. The vessel boundaries are enhanced by using the LoG filter. In one embodiment, the output of the LoG filter is subtracted from the original image to get higher contrast between vessels and a background region.

In one embodiment, the preprocessing includes Central Vessel Reflex (lighter region at the center of the larger vessels) suppression. In one embodiment, the Central Vessel Reflex removal is accomplished by performing a morphological closing operation with a disk structuring element of 1 pixel diameter applied to an image.

Note that in one embodiment, the preprocessing includes performing noise removal, contrast enhancement and Central Vessel Reflex removal. However, in alternative embodiments, only a subset of these three operations is performed. In yet another embodiment, the preprocessing operations are optional.

After performing any preprocessing operations, processing logic performs a number of operations to the preprocessed image. The results of such operations is a set of grayscale images.

Figure 2B:
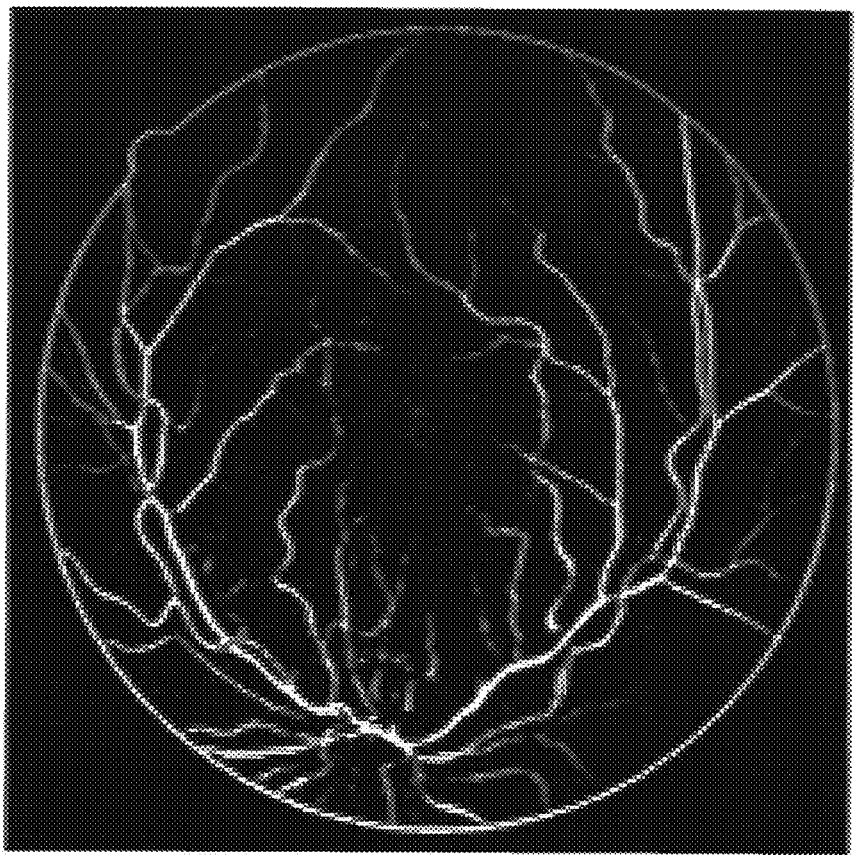
FIGS. 2A and B illustrate an original (preprocessed) image and the final high pass/normalized image according to one embodiment, respectively.
Figure 2A:
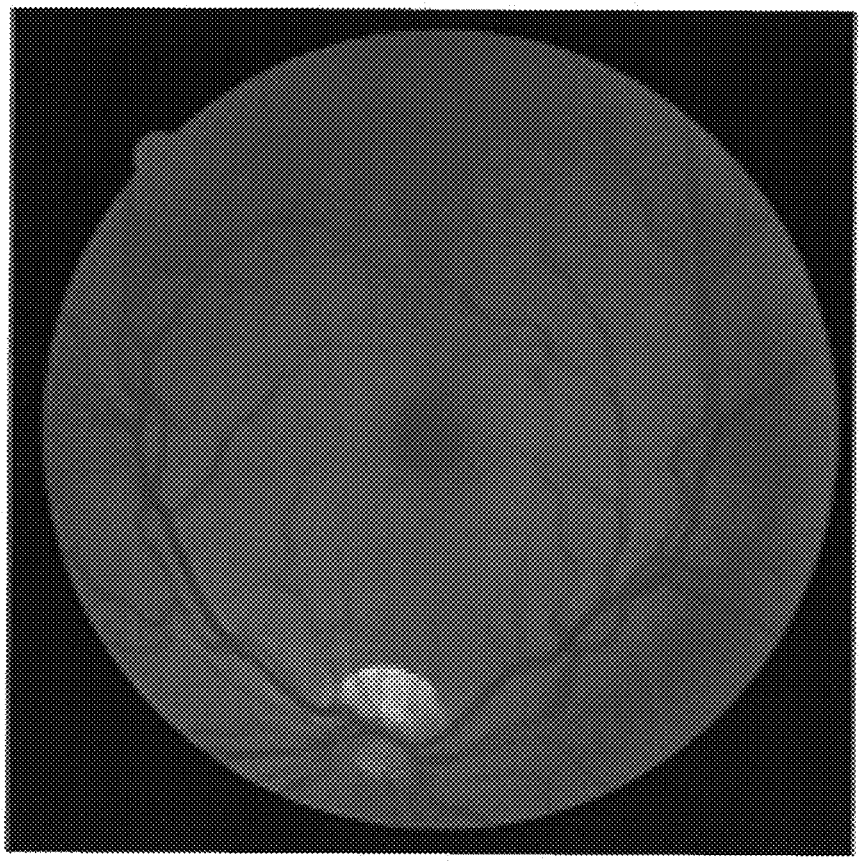

Referring back to FIG. 1, processing logic generates a normalized image from the preprocessed image (processing block 113). Image normalization is performed to enhance the vessels in retina images. In one embodiment, processing logic generates the normalized image by applying a median (high pass) filter with a large window to the preprocessed image to obtain a rough estimate of the background image. In one embodiment, the window is a 25×25 pixel window. Other sized windows may be used, such as, for example, 5×5, 50×50, depending on the base image size. For example, for an image of size approximately 500×500, a window of 25×25 is used. However, any large block size of image can be used, such 4-5% of the image size can be used. Processing logic then subtracts the preprocessed image from the background image resulting from applying the high pass filter. Vessels appear brighter in this high pass image. This subtracted image is then normalized to a zero mean and unit variance to enhance the vessels lying towards lower end of grey-levels. This normalization process involves subtracting a mean value from each of the pixels values, finding the variance among the pixel values that have undergone the subtraction operation and then dividing each of the pixel values by the variance. This normalization leads to discriminative enhancement of vessels and suppression of background. FIGS. 2A and B illustrate an original (preprocessed) image and the final high pass/normalized image, respectively.

Figure 3B:
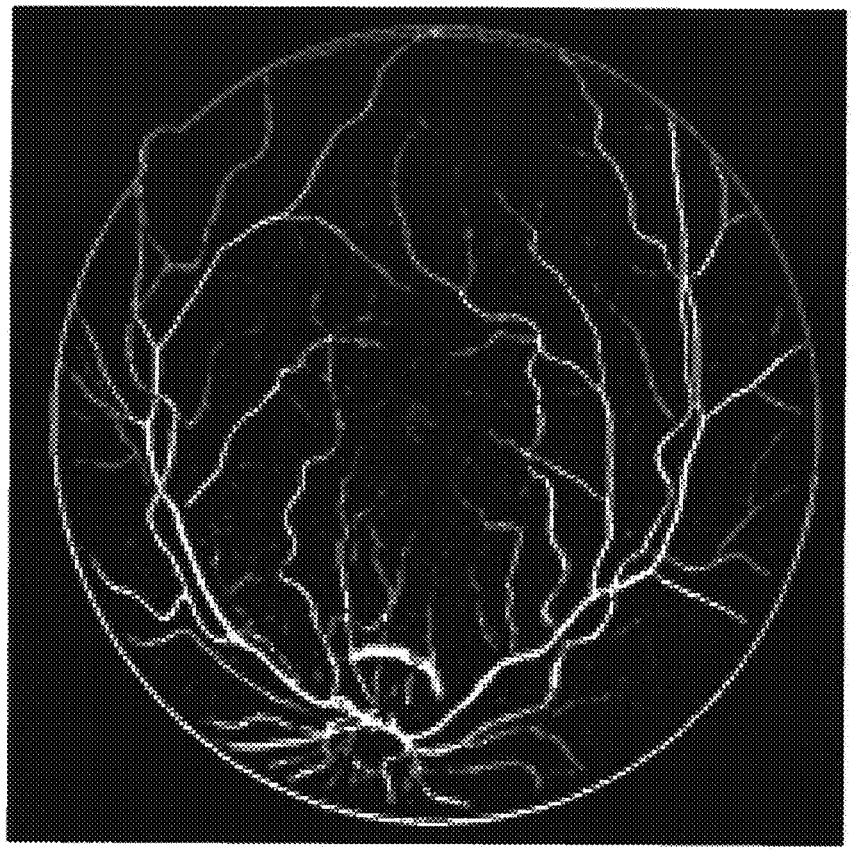
FIGS. 3A and B illustrate an original (preprocessed) image and its normalized Laplacian of Gaussian (LoG) filtered image according to one embodiment, respectively.
Figure 3A:
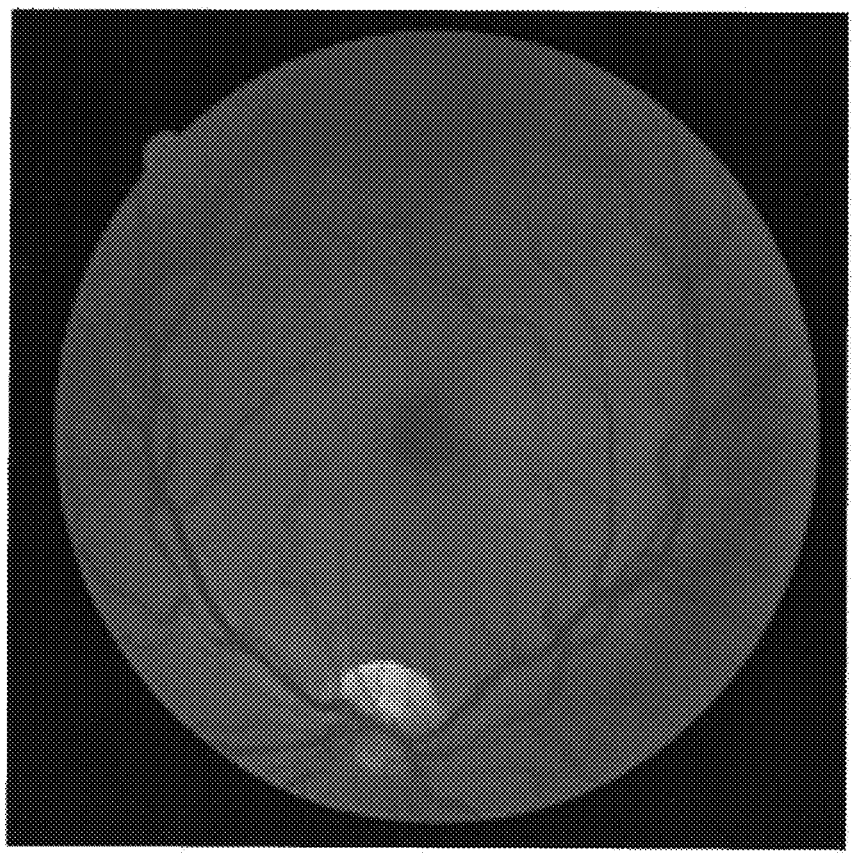

Processing logic also generates a LoG filtered image by applying a LoG filter to the preprocessed image (processing block 112). The LoG filter enhances vessel boundaries from the preprocessed image. The LoG filtered image has vessels at a higher intensity level than the background intensity of the preprocessed image. This LoG filtered image is normalized to zero mean and unit variance to increase contrast and utilize the complete span of gray values. FIGS. 3A and B illustrate an original (preprocessed) image and its normalized LoG filtered image, respectively.

Processing logic also generates a Frangi image by processing the preprocessed image (processing block 114). This processing is performed for Hessian based vesselness. Blood vessels can be considered as dark linear structures of different diameters and orientations on a brighter background. Frangi et al. (see Frangi, et. al, "Multiscale Vessel Enhancement Filtering," pp. 130-137. 1998) gave a relation in terms of eigenvalues of a Hessian matrix evaluated at different scales to compute a vesselness measure for blood vessels of different widths. A greater scale enhances only the big vessels, while a smaller scale enhances small vessels, big vessels as well as noise, where scale refers to the size of the kernel needed to blur the image such that vessels below a particular size are all blurred out. In one embodiment, a vesselness measure similar to that proposed by Frangi is used to find the likelihood of a pixel lying on a vessel. Specifically, to generate the Frangi vesselness image, two measures are generated for every pixel. These measures indicate the vessel nature are $F_1=L_1$ and $F_2=L_1^2+L_2^2$, where $L_1$ is the larger eigenvalue and $L_2$ is smaller eigenvalue, in absolute term, of the Hessian matrix, which is created at every pixel and includes the four derivatives. The two measures are then used to generate a vesselness measure at any point (pixel) according to the following formula:

$$F=(1-e^{-F_1})*(1-e^{-F_2}) \quad (1)$$

The result of calculating the above value for each pixel is used to form the Frangi vesselness image.

Processing logic also generates a line filtered image (processing block 116). In one embodiment, processing logic generates a line filtered image by applying a line filter over the Frangi vesselness image generated at processing block 114. The blood vessels in retina images can be approximated by connected linear structures. These linear structures have to be differentiated from bright blob-like structures in the images. Thus, the line filter is used because it takes advantage of the fact that the intensity of a blood vessel is concentrated along a line in a particular direction, in contrast to blob-like structures where the intensity is evenly distributed in all directions. The filter extracts segments exclusively based on their difference from blob-like structures having a similar intensity profile.

In one embodiment, it is assumed that intensity along a line segment (vessel) is more or less constant while there will be large intensity variations along the cross section of a line (vessel) beyond a certain width. Thus, the line strength at a pixel can be defined as the difference between the average of intensities along a line of fixed length and over a square of the same length, both centered at the same pixel with the same orientation. Since the line segment (vessel) can be oriented at any angle from the horizontal, this measure is calculated over a series of angles and the maximum response is chosen to be the strength of the line segment.

In one embodiment, the line strength over the entire angular range is denoted as $\max_x\{S_x=L_x-N_x\}$, over a series of angles, where $L_x$ is the mean intensity over the line kernel and $N_x$ is the mean intensity over the square kernel at the pixel x along a particular orientation. This is a way to find very fine lines because the thin vessels look like lines when investigated very closely.

The image that results from applying the line filter over the Frangi image is then normalized to a zero mean and unit variance to enhance the small vessels. Thereafter, in one embodiment, median filtering is performed over the normalized image to reduce noise and traces of central vessel reflex. The median filtered image is used as a mask over the Frangi image to reduce the floating speckles. In such a case, this mask is multiplied with the Frangi image. The resultant image retains the entire vessel region as in the original (preprocessed) image but noise and false positives are reduced by a large amount.

Figure 4C:
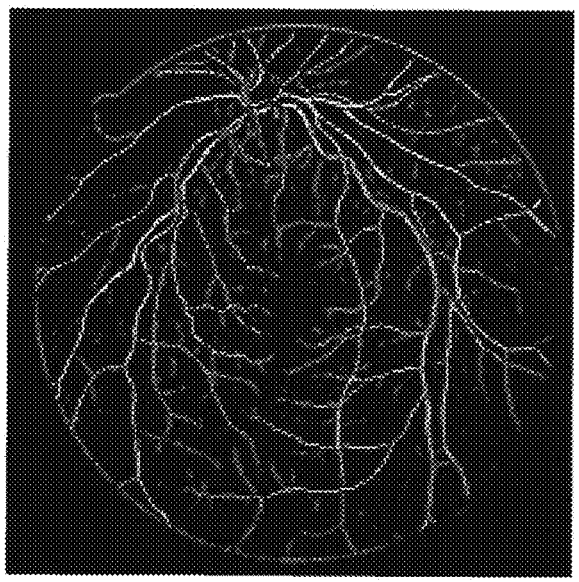
FIGS. 4A-C illustrate an example of an image, a Frangi vesselness image generated from the image in FIG. 4A according to one embodiment, and the output of line filtering applied on the Frangi image according to one embodiment, respectively.
Figure 4B:
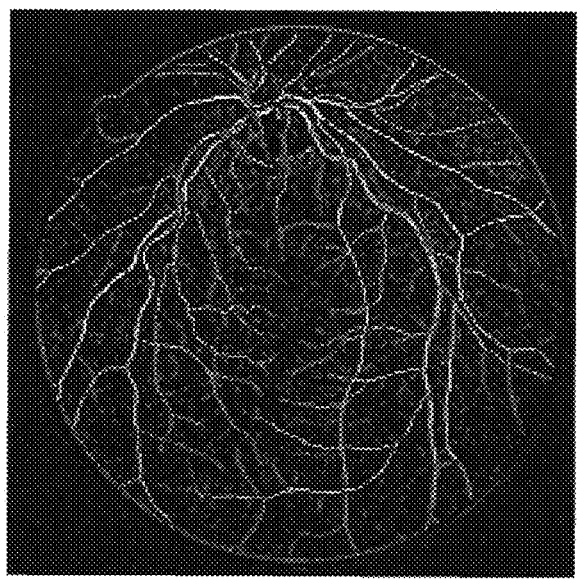
Figure 4A:
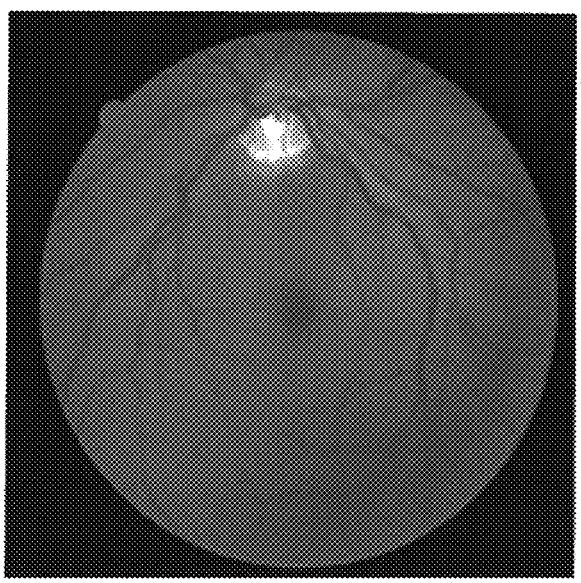

FIGS. 4A-C illustrate an example of an image, a Frangi vesselness image generated from the image in FIG. 4A, and the output of line filtering applied on the Frangi image, respectively.

Referring back to FIG. 1, the process of generating the multi-dimensional feature set further inputs applying Hu's moment to the high pass/normalized image generated in processing block 113 (processing block 115) and to the line filtered image generated in processing block 116 (processing block 117). The blood vessels in retina images are modelled as piecewise connected line segments of different length, width and orientation. Feature descriptors independent of these variations among lines can be used to identify vessels. Hu's invariant moments provide an excellent measure to identify vessels independent of the above mentioned features.

In one embodiment, for every pixel on the high/pass normalized and line filtered images, processing logic identifies a sub-image that is defined by taking a square window of fixed size around the pixel. In one embodiment, the size of this region is fixed to 17×17. For this sub-image, processing logic calculates Hu's moments. In one embodiment, the image moments are calculated as $$m_{pq} = \sum_i \sum_j i^p j^q I_{sub}(i,j) \quad (2)$$

where the summation goes over the sub-image $I_{sub}$. The corresponding central moments are defined as $$\Omega_{pq} = \sum_i \sum_j (i-\bar{i})^p (j-\bar{j})^q I_{sub}(i,j) \quad (3)$$

where $\bar{i}=m_{10}/m_{00}$, $\bar{j}=m_{01}/m_{00}$ refer to the coordinates of center of gravity of sub-image. The normalized central moments of order (p+q) are defined as, $\eta_{pq}=\Omega_{pq}/\Omega_{00}^\gamma$ where $\gamma=1+(p+q)/2$.

Hu's invariant moments can be derived from combinations of normalized central moments. In one embodiment, only the first two Hu's moment are used for vessel detection.

$$\Phi_1 = \eta_{20} + \eta_{02} \quad (4)$$

$$\Phi_2 = (\eta_{20} - \eta_{02})^2 + 4\eta_{11}^2 \quad (5)$$

In one embodiment, prior to calculating Hu's moments for the high pass/normalized image, processing logic performs area thresholding over the image to reduce stray noisy marks in image before feeding it to the moment generation subroutine. This feature provides a very nice estimate of the skeleton of blood vessels but has the potential to reduce the overall accuracy due to suppression of thin vessels. To avoid this, processing logic adds the line filtered image (prior to normalization) to the output of the Hu's moment based feature image (processing block 118) and adds the resultant image to the feature set.

Figure 5D:
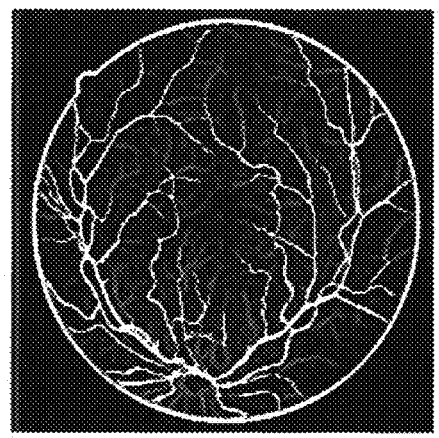
FIGS. 5A-B depict Hu's first and second moment on the high pass/normalized image according to one embodiment, respectively.
FIGS. 5C and D depict the same images depicted in FIGS. 5A and 5B, respectively, after addition of line filtered image according to one embodiment.
Figure 5C:
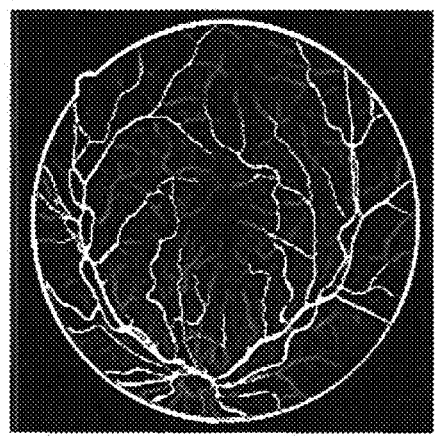
Figure 5B:
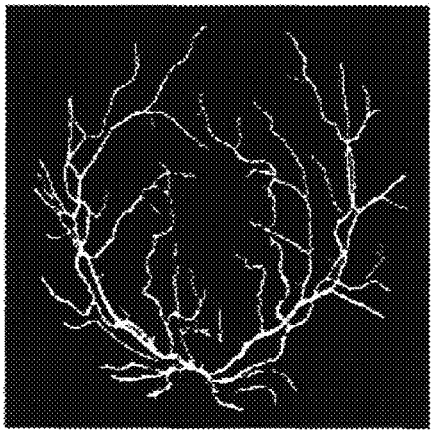
Figure 5A:
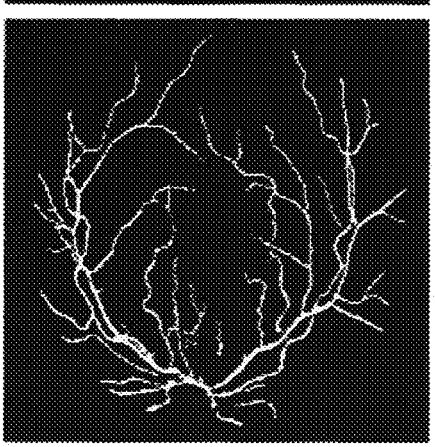

FIGS. 5A-B depict Hu's first and second moment on the high pass/normalized image, respectively. FIGS. 5C and D depict the same images depicted in FIGS. 5A and 5B, respectively, after addition of line filtered image.

Processing logic also identifies the X and Y coordinates for each pixel (processing block 111) from original (preprocessed) image to enable feature vectors to be created along with the pixel values from each of the images produced, namely, the LoG filtered image from processing block 112, the high pass/normalized image from processing block 113, the Frangi image from processing block 114, the line filtered image from processing block 116, the image resulting from multiplying the line filtered image from processing block 116 with the Frangi image from processing block 114, and the two images generated from the high pass/normalized image from processing block 113 and the line filtered image from processing block 116 for which Hu's moments were generated. In one embodiment, these images are all gray scale images. This represents feature space 120.

Figure 6:
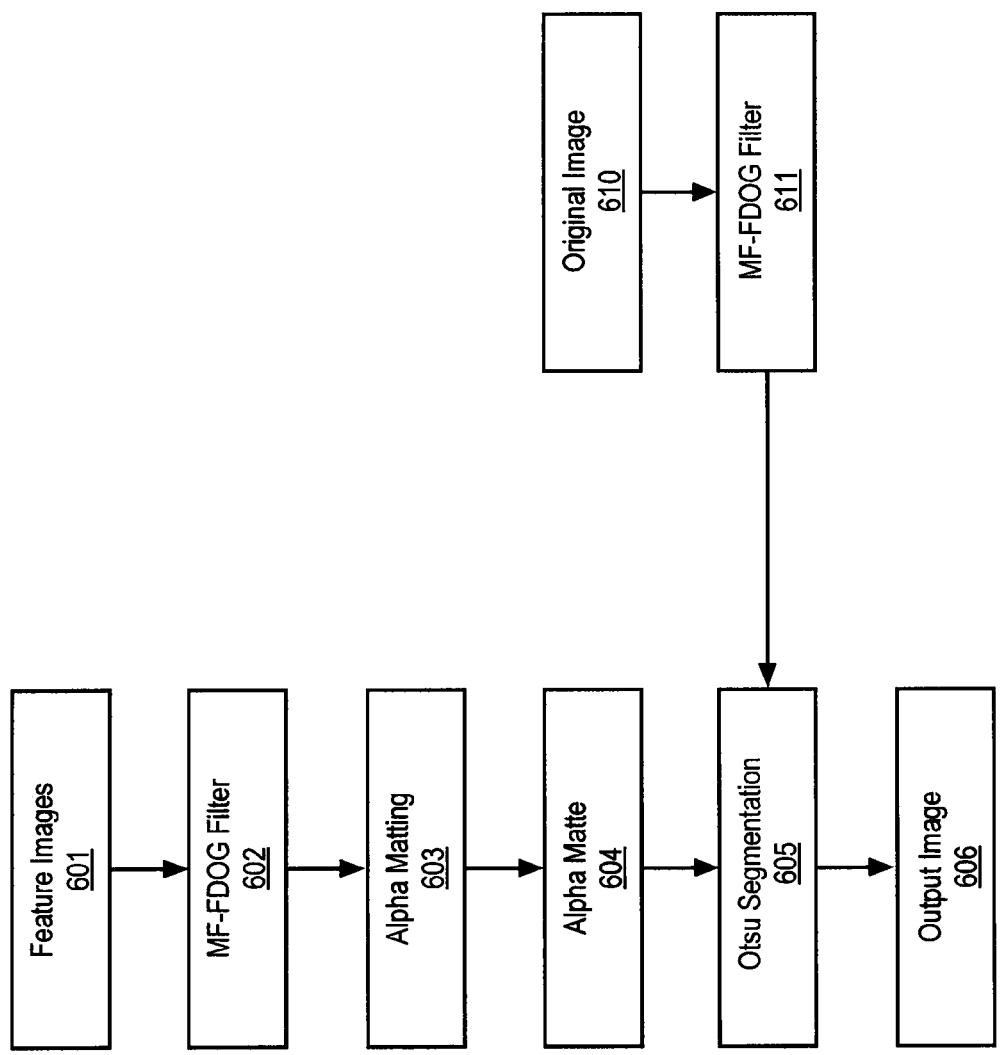
FIG. 6 is a flow diagram of one embodiment of the vessel extraction process.

Once created, processing logic feeds feature space 120, which is the multi-dimensional feature set, into the rest of the vessel extraction process. FIG. 6 is a flow diagram of one embodiment of the vessel extraction process. The process is performed by processing logic that may comprise hardware (circuitry, dedicated logic, etc.), software (such as is run on a general purpose computer system or a dedicated machine), firmware, or a combination of the three.

Referring to FIG. 6, processing logic receives feature images 601 of the feature space and applies a matched filter with first-order derivative of the Gaussian (MF-FDOG) to the images (processing block 602). Processing logic also applies the MF-FDOG filter to the original (preprocessed) image 610 (processing block 611).

Processing logic then performs alpha matting to the image data of the images (processing block 604). In one embodiment, the alpha matting is K-nearest neighbor (KNN)-alpha matting.

Using the alpha matte 604 produced by performing alpha matting and the filter image from processing block 611, processing logic performs Otsu segmentation (processing block 605) and produces output image 606, which is an image of the delineated block vessels.

KNN-Matting

Alpha matting refers to the process of separating an image into foreground and background components and obtaining a corresponding opacity mask. The opacity mask is commonly called the alpha matte and its value is obtained for each individual pixel in the image. Typically, for a grayscale image $$I(i,j) = \alpha F(i,j) + (1-\alpha) B(i,j) \quad (6)$$

where I(i,j) is the image intensity at pixel (i,j), F is the foreground and B is the background image. At each pixel, the value of three unknowns $\{\alpha, F, B\}$ is calculated from one equation. Consequently, the alpha matting problem is highly under constrained. A user could provide a tri-map or scribbles which can be used to identify known foregrounds and backgrounds. However, additional constraints are still needed to solve the problem. KNN matting uses the multi-dimensional feature space and works on non-local principle for finding neighbors. It is advantageous because it does not need large kernels to search for similar pixels in the neighborhood and provides a closed form solution.

The non-local principle is based on the idea that alpha matte at a pixel is the weighted sum of alpha values of pixels with similar appearance in a non-local neighborhood. The weights are defined by a kernel function and are based on distances computed from the multi-dimensional features according to:

$$E[\alpha_x] \approx \frac{\sum_y \alpha_y k(x,y)}{\sum_y k(x,y)} \quad (7)$$

which can be expressed as $d_x \alpha_x k(x,.)^T \Lambda$, where $k(x,y)$ is the similarity between $\alpha$ values at location x and y, $d_x = \Sigma_y k(x,y)$ and $\Lambda$ is the vector of all $\alpha$ values over the image. Let $\{A|\alpha(x,y) k(x,y)\}$ be the N×N similarity matrix where N is the number of pixels and $D = \text{diag}(d_i)$ be an N×N diagonal matrix. Then the expectation in Eq. 7 can be written jointly as $$D\Lambda \approx A\Lambda \quad (8)$$

$$(D-A)\Lambda \approx 0 \quad (9)$$

$$\Lambda^T L_c \Lambda = 0 \quad (10)$$

where $L_c = (D-A)^T(D-A)$ is called the clustering Laplacian. This solution leads to minimizing the squared difference $\Sigma_y A_{xy}(\alpha_x - \alpha_y)^2$. The kernel function can now be defined as $k(x,y) = 1 - \|F(x) - F(y)\|$, where F is the normalized feature vector. This linear kernel function provides soft segmentation. Rather than using $L_c = (D-A)^T(D-A)$, in one embodiment, $L_c = (D-A)$ is used, which is sparser and runs fast. In one embodiment, a pre-conditioned conjugate gradient is used to obtain a solution for $\alpha$. When the user specified tri-maps are given, the minimization can be written as $$(L + \lambda D)\Sigma_i^N \alpha_i = \lambda m,$$

where $D = \text{diag}(m)$ and m is a binary vector of indices of all the marked up pixels. In one embodiment, $\lambda$, is 1000 and measures the users confidence on markups. Other values may be used based on the application. For example, the value can be as low as 1.

Tri-Map Generation

As mentioned above, any matting problem needs user inputs in the form of sparse mark-ups. In one embodiment, the dominant vessels in the retina images are used to generate the tri-map automatically. The normalized high pass image consists of only dominant vessels and is used to create a skeleton for the vasculature. This skeleton acts as user scribbles for foreground area (vessels). In one embodiment, prior to using the normalized high pass image as a tri-map, optic cup removal is applied to the normalized high pass image.

Figure 7C:
FIGS. 7A-C illustrate a normalized image, an example of a foreground map generated by the procedure and a background map generated by this procedure according to one embodiment, respectively.
Figure 7B:
Figure 7A:
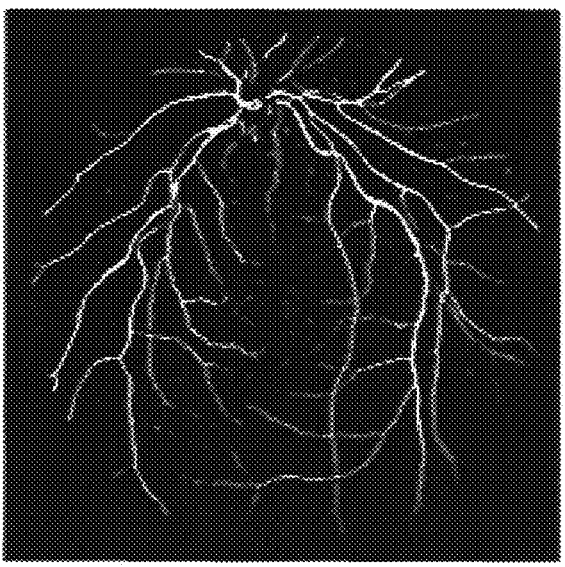

Morphological thinning operation and area thresholding are performed before using the high pass image as a tri-map. The known background areas are also determined from the same image. It is assumed that the normalized image covers most of the vasculature of the retina images. This image is dilated and the inverted image can then be used as the background mask. FIGS. 7A-C illustrate a normalized image, an example of a foreground map generated by the procedure and a background map generated by this procedure, respectively.

Segmentation

The feature images in multi-dimensional feature set contain traces of boundary of optic disc and eye due to their vessel like appearance. In one embodiment, a first order derivative of Gaussian (FDOG) filter is used to suppress these. Blood vessels have a gaussian like profile across their cross-section whereas the optic disk and other thick bright regions have intensity profile similar to a step function. The FDOG curve is anti-symmetric around its center value. Thus, the response to applying an FDOG filter is symmetric for bright optic disk and anti-symmetric for blood vessels. The local average of the response (equivalent to low pass filtering) typically returns a high value at the boundary of optic disk and minimal value for blood vessels. The inverted image of this response is used as mask, multiplied to the feature images in the multi-dimensional feature set.

For choosing a threshold value, the Otsu segmentation technique is used along with the locally averaged response output from the FDOG filter. The Otsu segmentation on alpha matte returns a threshold value which is added to the locally averaged response image output from the FDOG filter. The resulting image generated by adding the threshold value to the locally averaged response image output from the FDOG filter is then used as a reference threshold image, Every pixel in the resultant alpha matte is compared with the corresponding pixel in the reference image and a decision (binarize) is made based on whether the value in the reference image is higher or lower than a current pixel. This yields a relatively higher threshold value for false positives regions whereas other regions are compared against the normal value of Otsu segmentation technique.

Figure 8A:
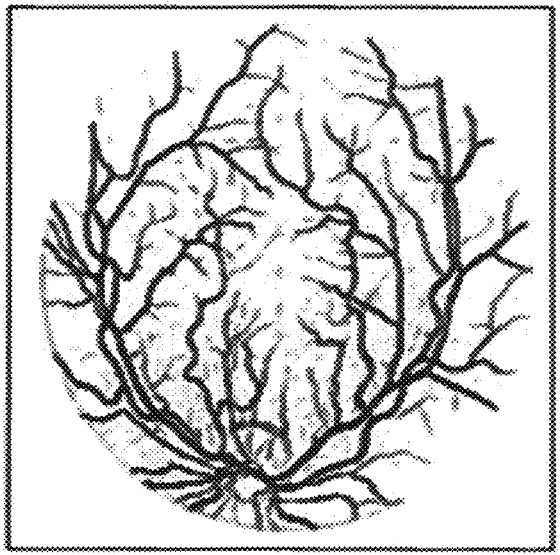
FIGS. 8A-C show an alpha matte, a thresholded image, and ground truth, respectively, according to one embodiment.
Figure 8B:
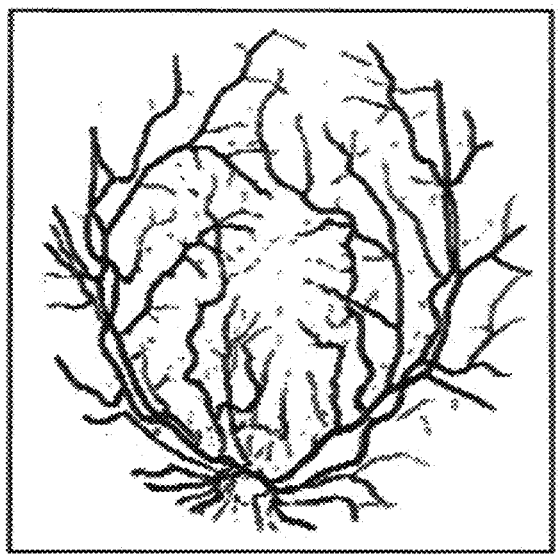
Figure 8C:
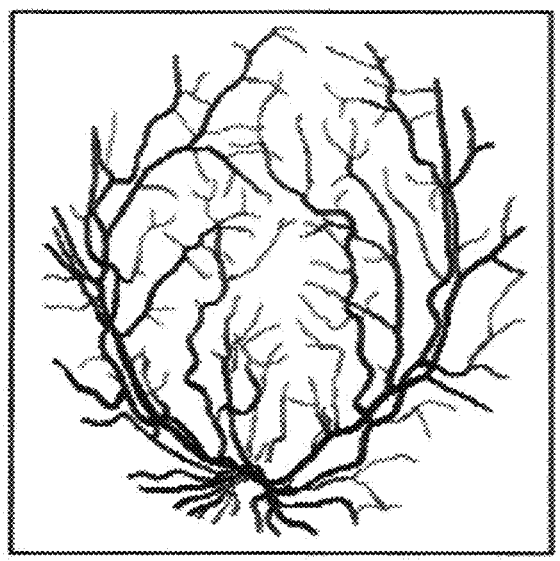

FIGS. 8A-C show an alpha matte, a thresholded image, and ground truth, respectively. As shown in FIGS. 8A-C, the alpha matte contains a prominent optic disk boundary which can be greatly reduced by the FDOG based thresholding technique.

Thus, a novel scheme of alpha matting to separate foreground from background for purposes of vessel extraction has been disclosed. The tri-map generation to generate the tri-map as part of the alpha matting is automated from the generated features. This serves skeleton for sure vessel region whereas background region is constructed from it. This is a huge step in the automatic extraction of blood vessel from retina color images, thus reducing the human involvement.

An Example of a Vessel Extraction System

Figure 9:
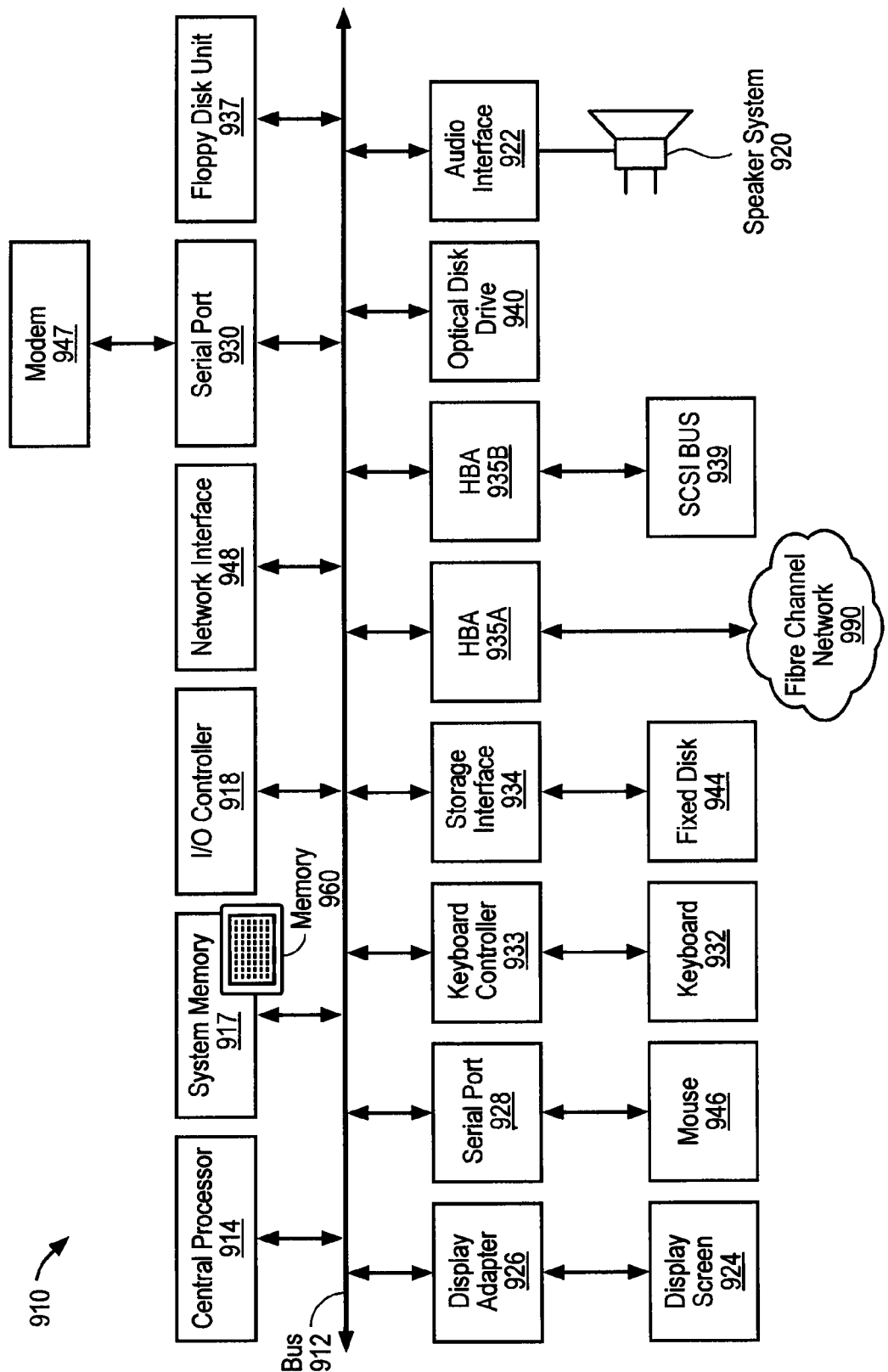
FIG. 9 depicts a block diagram of one embodiment of a vessel extraction system to perform operations for retinal vessel extraction.

FIG. 9 depicts a block diagram of a vessel extraction system. The vessel extraction system comprising a memory to store one or more images, such as an original image that is to undergo retinal vessel extraction and/or feature set images. The system also includes a processing unit that acts as a retinal vessel extractor to perform alpha matting on a multi-dimensional feature set derived from image data of a first image and perform retinal vessel extraction, including performing segmentation on the image by separating foreground and background image data from the first image using an output from the alpha matting. In one embodiment, the alpha matting comprises K-nearest neighbor (KNN) based alpha matting and the processing unit performs an Otsu segmentation process on the output of the alpha matting.

Referring to FIG. 9, vessel extraction system 910 includes a bus 912 to interconnect subsystems of vessel extraction system 910, such as a processor 914, a system memory 917 (e.g., RAM, ROM, etc.), an input/output controller 918, an external device, such as a display screen 924 via display adapter 926, serial ports 928 and 930, a keyboard 932 (interfaced with a keyboard controller 933), a storage interface 934, a floppy disk drive 937 operative to receive a floppy disk 938, a host bus adapter (HBA) interface card 935A operative to connect with a Fibre Channel network 990, a host bus adapter (HBA) interface card 935B operative to connect to a SCSI bus 939, and an optical disk drive 940. Also included are a mouse 946 (or other point-and-click device, coupled to bus 912 via serial port 928), a modem 947 (coupled to bus 912 via serial port 930), and a network interface 948 (coupled directly to bus 912).

Bus 912 allows data communication between central processor 914 and system memory 917. System memory 917 (e.g., RAM) may be generally the main memory into which the operating system and application programs are loaded. The ROM or flash memory can contain, among other code, the Basic Input-Output system (BIOS) which controls basic hardware operation such as the interaction with peripheral components. Applications resident with computer system 910 are generally stored on and accessed via a computer readable medium, such as a hard disk drive (e.g., fixed disk 944), an optical drive (e.g., optical drive 940), a floppy disk unit 937, or other storage medium.

Storage interface 934, as with the other storage interfaces of computer system 910, can connect to a standard computer readable medium for storage and/or retrieval of information, such as a fixed disk drive 944. Fixed disk drive 944 may be a part of computer system 910 or may be separate and accessed through other interface systems.

Modem 947 may provide a direct connection to a remote server via a telephone link or to the Internet via an internet service provider (ISP). Network interface 948 may provide a direct connection to a remote server that may perform one or more of the operations described herein. Network interface 948 may provide a direct connection to a remote server via a direct network link to the Internet via a POP (point of presence). Network interface 948 may provide such connection using wireless techniques, including digital cellular telephone connection, a packet connection, digital satellite data connection or the like.

Many other devices or subsystems (not shown) may be connected in a similar manner (e.g., document scanners, digital cameras and so on). Conversely, all of the devices shown in FIG. 9 need not be present to practice the techniques described herein. The devices and subsystems can be interconnected in different ways from that shown in FIG. 9. The operation of a computer system such as that shown in FIG. 9 is readily known in the art and is not discussed in detail in this application.

Code to implement the vessel extraction operations described herein can be stored in non-transitory computer-readable storage media such as one or more of system memory 917, fixed disk 944, optical disk 942, or floppy disk 938. The operating system provided on computer system 910 may be MS-DOS®, MS-WINDOWS®, OS/2®, UNIX®, Linux®, or another known operating system.

Figure 10:
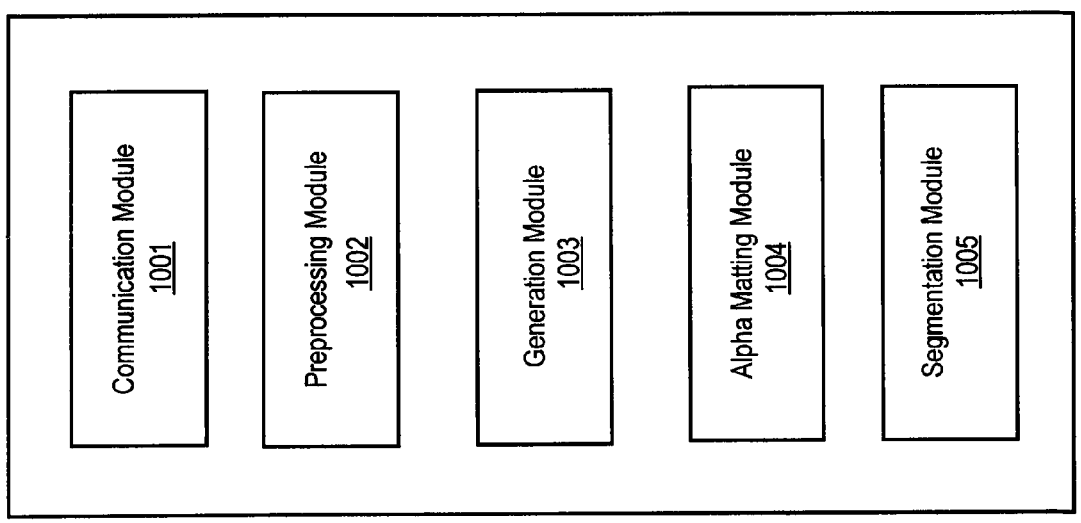
FIG. 10 illustrates a set of code (e.g., programs) and data that is stored in memory of one embodiment of a system.

FIG. 10 illustrates a set of code (e.g., programs) and data that is stored in memory of one embodiment of a retinal vessel extraction system, such as the system set forth in FIG. 9. The vessel extraction system uses the code, in conjunction with a processor, to implement the necessary operations (e.g., logic operations) to implement the described herein.

Referring to FIG. 10, the memory stores a communication module 1001 used for performing communication to receive the original images that are to undergo vessel extraction. The memory also a preprocessing module 1002 to perform one or more preprocessing operations, such as those described above, on the original images. The memory further includes a feature set generation module 1003 which when executed by a processor is responsible for generating the image data for the multi-dimensional feature set as described above. The memory also stores an alpha matting module 1004 which, when executed by a processor, is responsible for performing alpha matting (e.g., KNN-based alpha matting), including tri-map generation. The memory also stores segmentation module 1005 which, when executed by a processor, is responsible for performing segmentation (e.g., Otsu segmentation).

The code is stored in a non-transitory computer-readable storage medium such as system memory 917, fixed disk 944, optical disk 942 or floppy disk 948 of the system in FIG. 9.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A method comprising:
   performing alpha matting on a multi-dimensional feature set derived from image data of a first image, wherein the multi-dimensional feature set is derived by generating a Frangi image from the first image, applying line filtering to the Frangi image to create a line filtered image and multiplying the line filtered image with the Frangi image; and
   performing retinal vessel extraction, including performing segmentation on the image by separating foreground and background image data from the first image using an output from the alpha matting.

2. The method defined in claim 1 wherein the alpha matting comprises K-nearest neighbor (KNN) based alpha matting.

3. The method defined in claim 1 wherein performing retinal vessel extraction comprises performing an Otsu segmentation process to the output of the alpha matting.

4. The method defined in claim 3 further comprising:
   applying a matched filter with first-order derivative of the Gaussian (MF-FDOG) filter to the first image to create a filtered image; and
   adding a reference image resulting from the Otsu segmentation process to the filtered image.

5. The method defined in claim 1 further comprising generating the multi-dimensional feature set by applying one or more of operations of a set of operations on the image data of the first image or data derived from the image data of the first image, the set of operations including:
   generating a filtered image by applying a Laplace of Gaussian (LoG) filter to the first image;
   generating a normalized image from the first image;
   calculating Hu's moments on the line filtered image; and
   calculating Hu's moments on the normalized image.

6. The method defined in claim 5 wherein applying one or more of a set of operations comprises applying all operations in the set of operations.

7. The method defined in claim 1 further comprising applying a matched filter with first-order derivative of the Gaussian (MF-FDOG) filter to a plurality of feature images derived from the image data of the image.

8. The method defined in claim 1 further comprising preprocessing the image data of the image prior to generating the multi-dimensional feature set.

9. The method defined in claim 8 wherein preprocessing the image data includes one or more of: performing noise removal on the image data, performing contrast enhancement on the image data, and performing Central Vessel Reflex removal on the image data.

10. An article of manufacture having one or more non-transitory computer readable storage media storing instructions thereon which, when executed by a system, cause the system to perform a method comprising:

performing alpha matting on a multi-dimensional feature set derived from image data of a first image, wherein the multi-dimensional feature set is derived by generating a Frangi image from the first image, applying line filtering to the Frangi image to create a line filtered image and multiplying the line filtered image with the Frangi image; and performing retinal vessel extraction, including performing segmentation on the image by separating foreground and background image data from the first image using an output from the alpha matting.

11. The article of manufacture defined in claim 10 wherein the alpha matting comprises K-nearest neighbor (KNN) based alpha matting.

12. The article of manufacture defined in claim 10 wherein performing retinal vessel extraction comprises performing an Otsu segmentation process to the output of the alpha matting.

13. The article of manufacture defined in claim 12 wherein the method further comprises:

applying a matched filter with first-order derivative of the Gaussian (MF-FDOG) filter to the first image to create a filtered image; and adding a reference image resulting from the Otsu segmentation process to the filtered image.

14. The article of manufacture defined in claim 10 wherein the method further comprises generating the multi-dimensional feature set by applying one or more of operations of a set of operations on the image data of the first image or data derived from the image data of the first image, the set of operations including:

generating a filtered image by applying a Laplace of Gaussian (LoG) filter to the first image;

generating a normalized image from the first image;

calculating Hu's moments on the line filtered image; and calculating Hu's moments on the normalized image.

15. The article of manufacture defined in claim 14 wherein applying one or more of a set of operations comprises applying all operations in the set of operations.

16. The article of manufacture defined in claim 10 wherein the method further comprises applying a matched filter with first-order derivative of the Gaussian (MF-FDOG) filter to a plurality of feature images derived from the image data of the image.

17. The article of manufacture defined in claim 10 wherein the method further comprises preprocessing the image data of the image prior to generating the multi-dimensional feature set.

18. The article of manufacture defined in claim 17 wherein preprocessing the image data includes one or more of: performing noise removal on the image data, performing contrast enhancement on the image data, and performing Central Vessel Reflex removal on the image data.

19. A system comprising:

a memory to store an image; and a retinal vessel extractor coupled to the memory to perform alpha matting on a multi-dimensional feature set derived from image data of a first image and perform retinal vessel extraction, including performing segmentation on the image by separating foreground and background image data from the first image using an output from the alpha matting, wherein the multi-dimensional feature set is derived by generating a Frangi image from the first image, applying line filtering to the Frangi image to create a line filtered image and multiplying the line filtered image with the Frangi image.

20. The system defined in claim 19 wherein the alpha matting comprises K-nearest neighbor (KNN) based alpha matting, and further wherein retinal vessel extractor performs an Otsu segmentation process on the output of the alpha matting.

* * * * *